(12) United States Patent
Nagasaka

(10) Patent No.: US 8,904,627 B2
(45) Date of Patent: Dec. 9, 2014

(54) METHOD FOR SEALING PACKAGE

(75) Inventor: Kimio Nagasaka, Hokuto (JP)

(73) Assignee: Seiko Epson Corporation (JP)

( * ) Notice: Subject to any disclaimer, the term of this patent is extended or adjusted under 35 U.S.C. 154(b) by 155 days.

(21) Appl. No.: 13/567,375

(22) Filed: Aug. 6, 2012

(65) Prior Publication Data

US 2013/0047417 A1 Feb. 28, 2013

(30) Foreign Application Priority Data

Aug. 29, 2011 (JP) .................................. 2011-186420
Jun. 12, 2012 (JP) .................................. 2012-132708

(51) Int. Cl.
| | |
|---|---|
| *H01S 4/00* | (2006.01) |
| *H01L 21/50* | (2006.01) |
| *G01R 33/00* | (2006.01) |
| *H01L 23/10* | (2006.01) |
| *A61B 5/04* | (2006.01) |

(52) U.S. Cl.
CPC .............. *H01L 23/10* (2013.01); *H01L 21/50* (2013.01); *G01R 33/0047* (2013.01); *G01R 33/0076* (2013.01); *A61B 2562/242* (2013.01); *A61B 5/04008* (2013.01); *A61B 5/04007* (2013.01)
USPC ......... 29/592.1; 29/428; 29/527.2; 29/890.09

(58) Field of Classification Search
USPC ......... 29/592.1, 428, 527.2, 890.09; 310/344, 310/370
See application file for complete search history.

(56) References Cited

U.S. PATENT DOCUMENTS 7,279,824 B2 * 10/2007 Tanaya et al. ................. 310/344
7,557,491 B2 * 7/2009 Kigawa et al. ................ 310/344

FOREIGN PATENT DOCUMENTS

| JP | 61-051746 | 3/1986 |
|---|---|---|
| JP | 2008-057995 | 3/2008 |
| JP | 2008-103184 | 5/2008 |

* cited by examiner

*Primary Examiner* — Thiem Phan
(74) *Attorney, Agent, or Firm* — Harness, Dickey & Pierce, P.L.C.

(57) ABSTRACT

An ampoule is disposed within a package, a metal tube is disposed between the package and a lid, one end of the metal tube protrudes to the outside, and a low melting point glass having a through-hole is disposed between the package and lid in order to connect the package and the lid each other. An end of the metal tube is connected to a pump which controls circulation of a cleaning solvent or coating agent. The pump circulates the cleaning solvent or the coating agent between the inside and the outside of the package. The gap between the package and the lid formed when the metal tube is extracted by and extracting melting the low melting point glass is sealed.

5 Claims, 9 Drawing Sheets

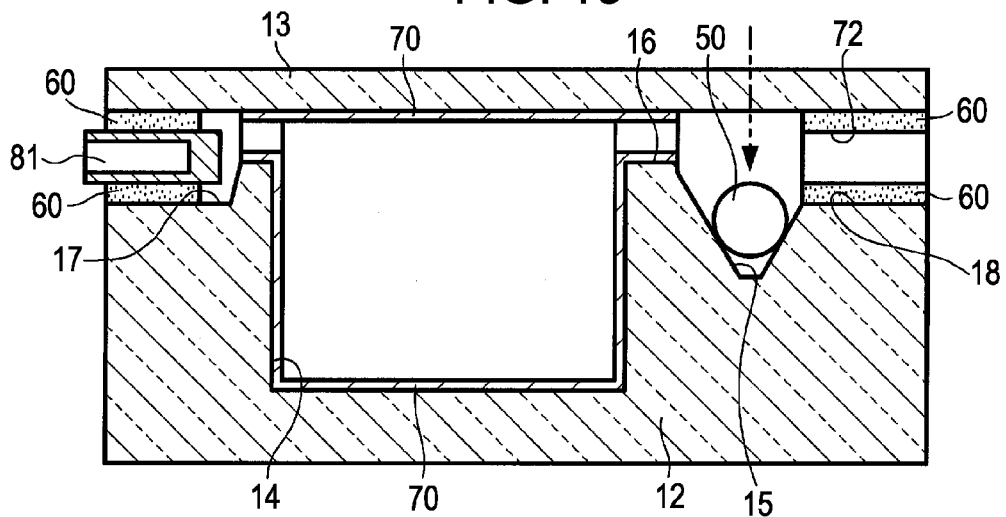
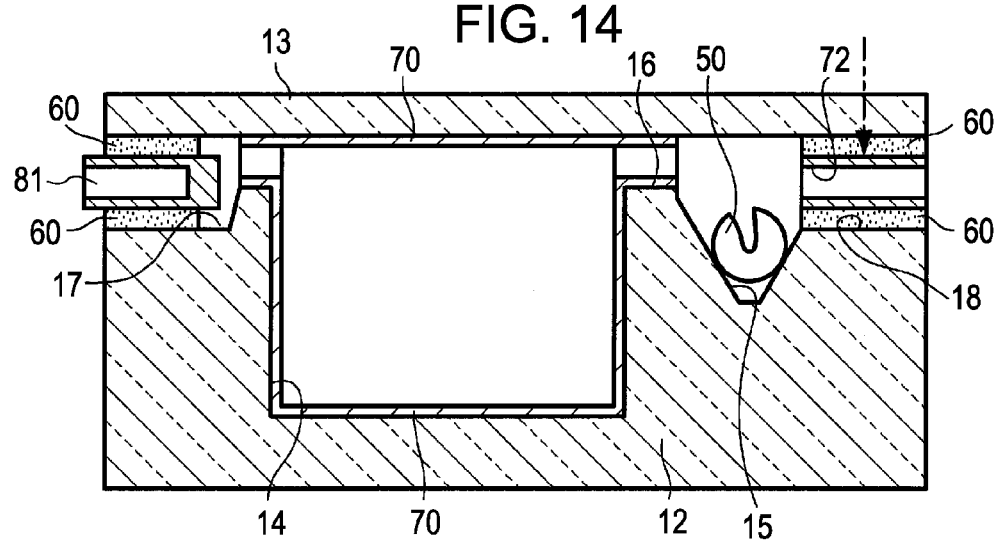
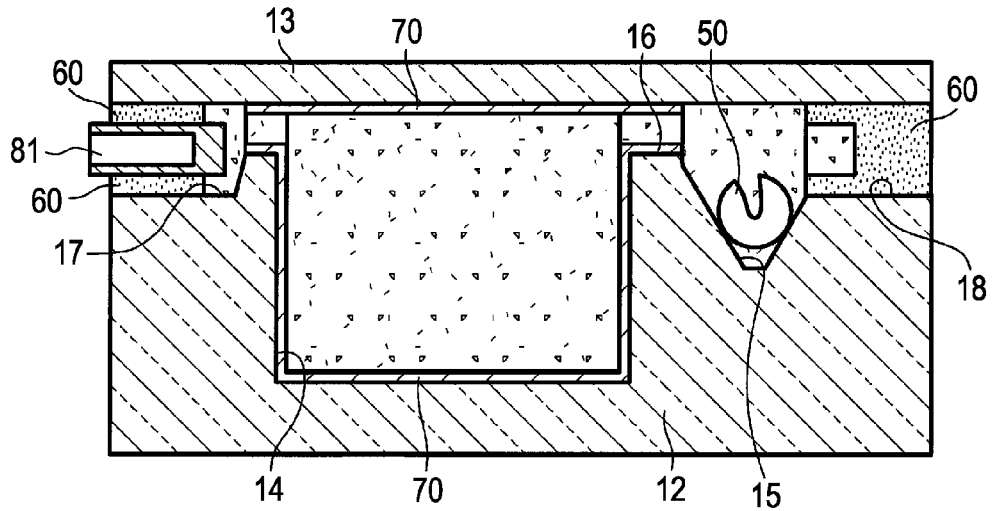

METHOD FOR SEALING PACKAGE

BACKGROUND

1. Technical Field

The present invention relates to a method for sealing a package.

2. Related Art

A technique which seals electric components and a semiconductor has been known. For example, JP-A-2008-103184 discloses a method that seals a space between a front panel and a rear panel by disposing a sealing member in a vent and by melting a sealing member which applied to a laser beam in order to achieve a display apparatus such as a plasma display (PDP), a field emission display (FED) and the like. JP-A-2008-57995 discloses a method that seals a through-hole by disposing the sealing member in the through-hole formed on the bottom of a container and by melting the sealing member which is applied to the irradiation of a laser beam. JP-A-61-51746 discloses a method that performs hermetic sealing by heating and melting the surrounding glass of a micropore using a laser beam to close the micropore after forming the micropore within a cylindrical glass tube and performing exhausting and enclosure of gas via the micropore.

As an apparatus that generates a magnetic field from the heart of a living body and the like, an optical pumping type magnetic sensor has been known. The magnetic sensor utilizes gas cells enclosing an alkali metal gas. In a case where the gas cells are manufactured, a package of the gas cells is formed and the coating agent is introduced into the package to form a film in an inner face of the package. In the methods of the above-mentioned JPA-2008-103184 or JP-A-2008-57995, since a sealing member seals a through-hole of the package, it is difficult for the coating agent to be introduced into an inner face of the package. In the method disclosed in JP-A-61-51746, in order to seal the micropores of a cylindrical glass tube, since it is necessary to heat the cylindrical glass tube to a high temperature, it is difficult to seal the package.

SUMMARY

An advantage of some aspects of the invention is a package may be easily sealed while making a fluid flow more easily between the inside and outside of a package.

According to an aspect of the invention, there is provided a method for sealing a package including: connecting a package and a lid by disposing a reception section receiving an alkali metal atom within an package having an opening, providing a tubular member having a first through-hole between the package and the lid covering the opening, the one end of the tubular member protruding outward, providing a first sealing member between the tubular member and the package or the lid, and providing a second sealing member having a second through-hole between the package and the lid; connecting fluid machinery connected to an end of the tubular member to control circulation of the fluid, introducing a coating agent into the inner face of the package via the second through-hole using the fluid machinery, forming film in the inner face of the package using the coating agent and exhausting the agent provided in the inner face of the package to the outside via the second through-hole using the fluid machinery; sealing a gap between the package and the lid formed when the tubular member is extracted by melting the first sealing member; and sealing the second through-hole by melting the second sealing member; and destroying the reception section by applying a laser beam to the reception section.

According to the method for sealing the package, it may be easy to provide the package in which the film is formed on an inner face thereof using the coating agent and encloses alkali metal atom.

It is preferable that, in the circulation, when the second through-hole is disposed in the coating agent to perform inflow of the coating agent, the fluid machinery exhausts gas within the package to the outside from the first through-hole to decrease pressure within the package.

According to the method for sealing the package, it is possible to introduce the coating agent into the inside of the package in a short time.

It is preferable that, in the connecting of the fluid machinery, when the coating agent flows out, the fluid machinery introduce gas compressed through the first through-hole into an inner face of the package to increase pressure within the package.

According to the method for sealing the package, it is possible to perform outflow of the coating agent from the inside of the package in a short time.

It is preferable that, in the connecting, the surface that connects the package and the lid is coated with the connection material, a rod-shaped member is disposed between the package and the lid and one end of the rod-shaped member is formed to protrude outward, the package and the lid are connected by the connection material being melted and the second sealing member may be formed by the connection material by extracting the rod-shaped member after cooling.

According to the method for sealing the package, it is easy to provide the second sealing member between the package and the lid.

It is preferable that, in the connecting, a surface that connects the package and the lid is coated with the connection material having a first temperature in a melting point, a material having a melting point of a second temperature higher than the first temperature is formed between the package and the lid, the second sealing member having the through-hole is disposed, the connection material is heated equal to or higher than the first temperature and less than the second temperature and the package and the lid are connected by melting the connection material, and in the sealing, the second sealing member may be heated below the second temperature.

According to the method for sealing the package, it is easy to provide the second sealing member between the package and the lid.

According to another aspect of the invention, there is provided a method for sealing a package including: disposing a tubular member having a through-hole between a package having an opening and a lid covering the opening and one end of the tubular member being formed to protrude to the outside, providing a sealing member between the tubular member and the package or the lid and connecting the package and the lid; connecting fluid machinery that controls circulation of the fluid to the one end of the tubular member and performing the circulation of the fluid via the through-hole between the inside and the outside of the package using fluid machinery; and extracting the tubular member and sealing a gap between the package and the lid formed when the tubular member is extracted by melting the first sealing member.

According to the method for sealing the package, it is easy to perform the circulation of the fluid between the outside and the inside of the package and the sealing of the package.

BRIEF DESCRIPTION OF THE DRAWINGS

The invention will be described with reference to the accompanying drawings, wherein like numbers reference like elements.

FIG. 13 is a view illustrating a manufacturing step of a gas cell according to a modified example 1.

FIG. 14 is a view illustrating a manufacturing step of a gas cell according to a modified example 1.

FIG. 15 is a view illustrating a manufacturing step of a gas cell according to a modified example 1.

DESCRIPTION OF EXEMPLARY EMBODIMENTS

1. EMBODIMENT

1. Configuration

Figure 1:
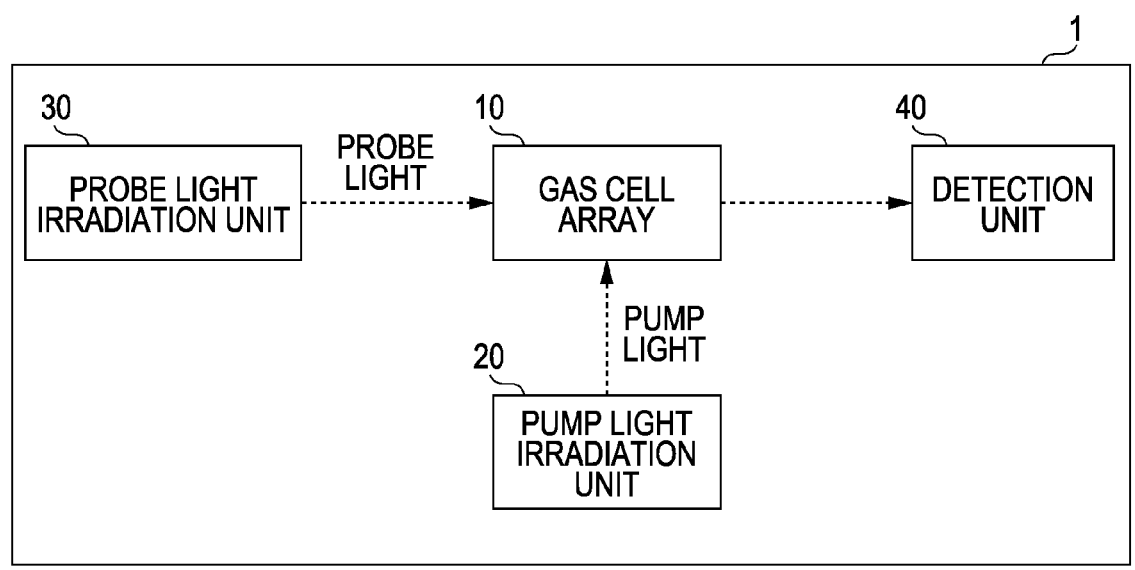
FIG. 1 is a block diagram showing a configuration of a magnetic measurement apparatus.

FIG. 1 is a block diagram showing a configuration of a magnetic measurement apparatus 1. The magnetic measurement apparatus 1 is a magnetic sensor that measures a magnetic field that is generated from the heart (magnetocardiography) and a magnetic field that is generated from the brain (magetoencephalography) as an index of a condition of a living body. The magnetic measurement apparatus 1 includes a gas cell array 10, a pump light irradiation unit 20, a probe light irradiation unit 30 and a detection unit 40. The gas cell array 10 has a plurality of gas cells 11. The gas cells 11 are enclosed with an alkali metal gas (for example, cesium (Cs)). The pump light irradiation unit 20 outputs a pump light (for example, light having a wavelength 894 nm corresponding to the inner diameter D1 ray of the cesium) that interacts with alkali metal atoms. A pump light has a circularly-polarized component. When the pump light is irradiated, a peripheral electron of the alkali metal atom is activated and a spin polarization is generated. Precession is caused in the alkali metal atom exposed to the spindle polarization by a magnetic field B generated by a measured object. The spin polarization of one alkali metal atom is alleviated with the passage of time.

However, since the pump light is a continuous wave (CW), the formation and the alleviation of the spin polarization are repeated to be parallel and continuously at the same time. Therefore, looking at the group of atoms as a whole, a normal spindle polarization occurs.

A probe light irradiation unit 30 outputs a probe light having a linearly polarized light. Before and after the transmission of the gas cell 11, the plane of the polarization of the probe light is rotated by the Faraday effect. The rotation angle of the polarization plane is a function of the magnetic field B. The detection unit 40 detects the rotation angle of the probe light. The detection unit 40 includes a light detection apparatus that detects a signal according to the amount of light of incident light, a processor that processes the light and a memory that stores data. The processor calculates the size of the magnetic field B using the signal output from the light detection apparatus. The processor writes the data indicating the calculated results to the memory. In this way, users can obtain information on the magnetic field B generated from a measured object.

Figure 2:
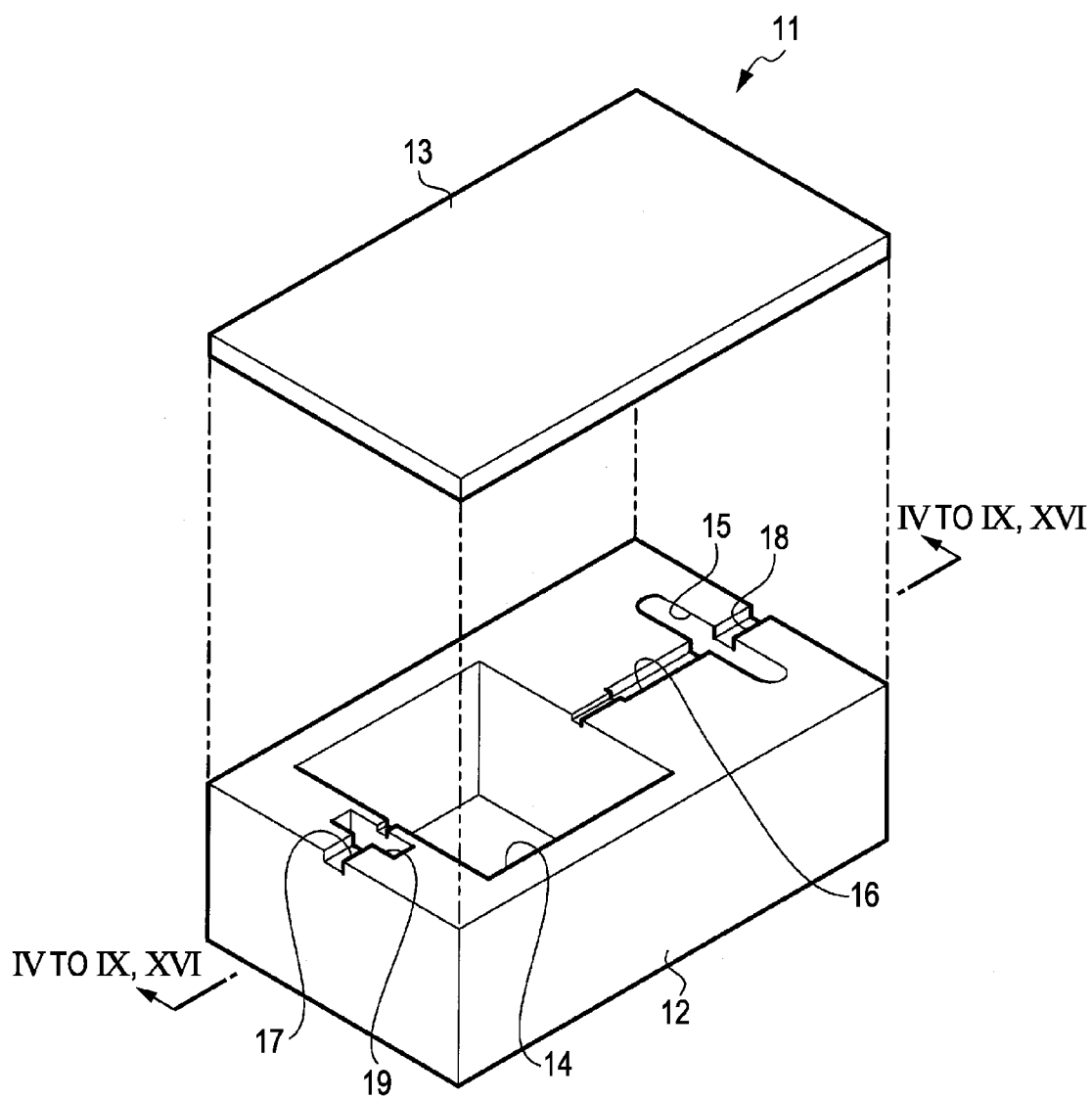
FIG. 2 is a perspective view showing a gas cell according to an embodiment.

FIG. 2 is a perspective view showing the gas cell 11. The gas cell 11 is formed by using a material having optical transparency, such as quartz glass or borosilicate glass and the like. The gas cell 11 includes a package 12 and a lid 13. The package 12, for example, is manufactured by a glass molding. In addition, the package 12 may be formed by a glass processing. The package 12 includes a main chamber 14 which encases the alkali metal gas. The main chamber 14 opens toward the outside. That is, the package 12 has an opening. The lid 13 is a lid covering the top of the package 12. The lid 13 is, for example, a flat plate of glass.

The package 12 is formed with a V-shaped concavity 15 in a cross-sectional view, which is adjacent to the main chamber 14. The concavity 15 accommodates an ampoule 50 that encloses the alkali metal. The ampoule 50 is, for example, a glass container. The ampoule 50 is used as a reception unit that receives the alkali metal atom. The top of package 12 is formed with a groove 16 being formed from the concavity 15 toward the main chamber 14. The groove 16 is also formed by the glass molding. The concavity 15 and the main chamber 14 are connected through the groove 16. The inner diameter of the groove 16 is a size that allows a cleaning solvent or the coating agent as described below to circulate. However, the inner diameter of the groove 16 may be a size that the alkali metal atom which has the spin polarization has a difficulty in entering the main chamber 14. In the groove 16 shown in FIG. 2, the inner diameter of the end of the main chamber 14 side is smaller than that of the end of the concavity 15 side. In addition, the top of the package 12 is formed with a groove 17 from the main chamber 14 toward the outside and formed with a groove 18 from the concavity 15 toward the outside. Furthermore, the top of the package 12 is formed with a V-shaped concavity 19 in a cross-sectional view so as to intersect the groove 17.

2. Manufacturing Method

Figure 3:
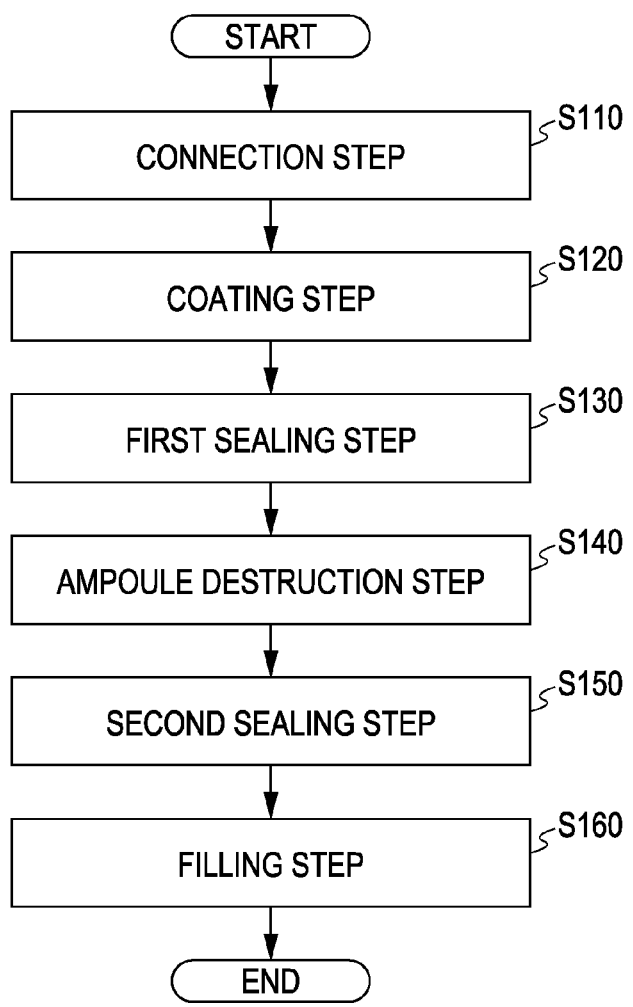
FIG. 3 is a flowchart showing a manufacturing step of a gas cell according to the embodiment.
Figure 4:
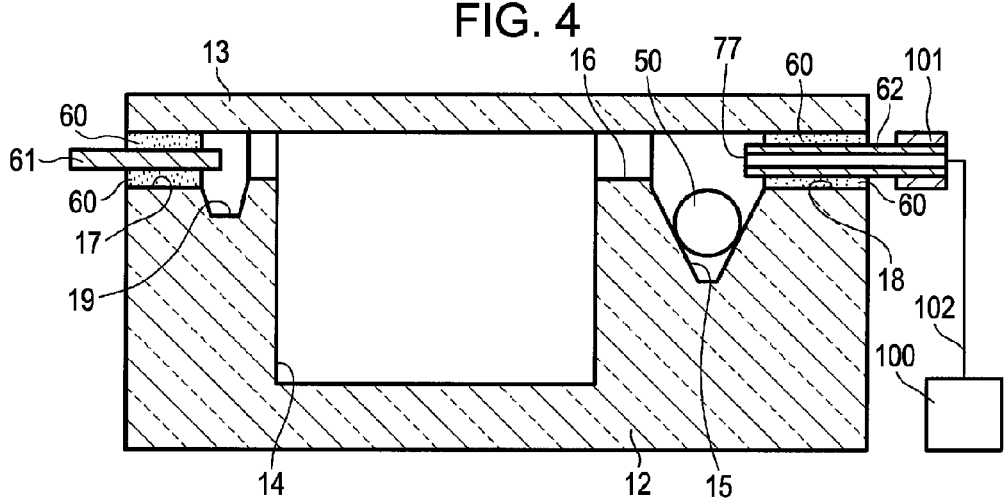
FIG. 4 is a view illustrating a manufacturing step of a gas cell according to the embodiment.

FIG. 3 is a flowchart showing a manufacturing step of the gas cell 11. FIGS. 4 to 9 are views illustrating a manufacturing step of the gas cell 11. FIGS. 4 to 9 are cross-sectional views of the gas cell 11 taken along line IV-IV to IX-IX of FIG. 2. In step S110 (connection step), the surface connected to the package 12 and the lid 13 is coated with a paste-formed low melting point glass 60. Specifically, a peripheral part of the upper surface of the package 12 and the lower surface of the lid 13 are coated with the paste-like low melting point glass 60. The coating agent of the low melting point glass 60 is for example, made by screen-printing or a dispenser. The coating agent of the low melting point glass 60 is followed by evaporation and drying of a solvent component included in the low melting point glass 60 using heating. Next, the concavity 15 of the package 12 is disposed on the ampoule 50. After the ampoule 50 is disposed, as shown in FIG. 4, a rod-shaped metal wire 61 is inserted into a groove 17. In this case, the metal wire 61 has one end thereof protruding to the outside and the other end thereof protruding to the concavity 19. In addition, a cylindrical metal tube 62 having a through-hole 77 is inserted into a groove 18. In this case, the metal wire 62 has one end thereof protruding to the outside and the other end thereof protruding to the concavity 15. The one end of the metal tube 62 is connected to a pump 100 via a pipe 102. The end of the metal tube 62 and the pipe 102 are connected by a coupler 101. The pump 100 has a function that controls pressure in the gas cell 11 by extracting the gas from the inside of the gas cell 11 or introducing a pressurized air into the inside of the gas cell 11. The metal tube 62 is formed by the metal that is not readily connectable to be in contact with the low melting point of the glass 60, for example, a material such as nickel and the like. In addition, it is not necessary that the whole portion of the metal tube 62 be formed of the metal that is not readily connectable to be in contact with the low melting point glass 60. For example, the metal tube 62 may perform nickel plating on the surface of the cylindrical member formed using the metal connecting to the low melting point glass 60. In addition, the package 12 is formed with the groove in which the metal wire 61 and the metal tube 62 are disposed so as to position the metal 61 and the metal tube 62.

The metal wire 61 and the metal tube 62 are disposed and then the lid 13 is overlapped on the package 12. Therefore, the metal wire 61 and the metal tube 62 are interposed between the package 12 and the lid 13 through the low melting point glass 60. That is, the low melting point glass 60 is disposed between the metal tube 62 and the package 12, and the metal tube 62 and the lid 13. Next, while pressing, the low melting point glass 60 is heated up to the temperature at which it melts, such as 400° C. In order to heat the low melting point glass, for example, an annealing oven is used. This heating enables the low melting point glass 60 between the package 12 and further enables the lid 13 to melt and the package 12 and the lid 13 to connect.

Figure 5:
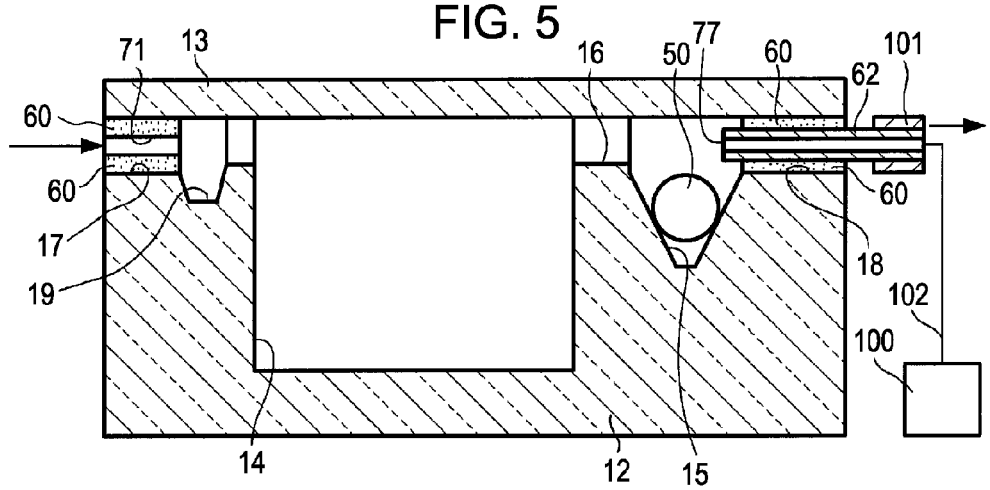
FIG. 5 is a view illustrating a manufacturing step of a gas cell according to the embodiment.

In addition, the melted low melting point glass 60 covers the circumferential surface of the metal wire 61 in the groove 17. However, the low melting point glass 60 overflowed from the groove 17 falls inside the concavity 19. Therefore, in the metal wire 61, one end protruding to the outside and the other end protruding to the concavity 19 are not covered by the low melting point glass 60. Therefore, the metal wire 61 passes through the low melting point glass 60 within the groove 17. In addition, the melted low melting point glass 60 covers the circumference surface of the metal tube 62 in the groove 18. However, the low melting point glass 60 overflowed from the groove 18 falls within the concavity 15. This prevents the low melting glass 60 from entering the through-hole 77 of the metal tube 62. After cooling, the metal wire 61 is extracted. When it is difficult to extract the metal wire 61, an ultrasonic vibration is applied to detach a coupling interface of the rod-shaped member and the connection material. Therefore, as shown in FIG. 5, the through-hole 71 is formed between the package 12 and the lid 13. In this case, the low melting point glass 60 forming the through-hole 71 is used as a second sealing member.

In step S120 (coating agent step), the gas cell 11 is put into the cleaning solvent. At this time, the gas cell 11 is disposed such that the through-hole 71 is put into the cleaning solvent.

For example, the gas cell 11 is disposed in a direction in which the through-hole 71 is directed downward. Next, a pump 100 introduces the gas in the gas cell 11 to the outside from the through-hole 77 to decrease a pressure in the gas cell 11. Therefore, the cleaning solvent is introduced into the inside of the gas cell 11 from the through-hole 71. The cleaning solvent cleans the inside of the gas cell 11 and then the pump 100 causes the gas compressed through the through-hole 77 to be introduced into the inside of the gas cell 11 to increase the pressure in the gas cell 11. Therefore, the cleaning solvent is introduced to the outside of the gas cell 11 from the through-hole 71.

Accordingly, a pollutant in the gas cell 11 is removed and then the coating agent is used to form the film 70 in the inside of the main chamber 14. The coating agent uses, for example, paraffin and silane-based hydrocarbon. The coating agent also may use hexamethyldisilane. A method for forming the film 70 is the liquid phase film formation method and the vapor phase film formation method. In either of the methods, in the same manner as the cleaning solvent, the gas cell 11 is disposed such that the through-hole 71 is placed in the coating agent and the coating agent is introduced from through-hole 71 and caused to flow out from the through-hole 71 by the pump 100. However, when utilizing the liquid phase film formation method, the coating agent is introduced into the gas cell 11 in liquid form. In this case, for example, the gas cell 11 is disposed in a direction in which the through-hole 71 directs downwardly. Meanwhile, when utilizing the vapor phase film formation method, the coating agent is introduced into the gas cell 11 in gas form. The cleaning fluid and the coating agent are fluid that circulates the inside and the outside of the gas cell 11 through the through-hole 71. In addition, pump 100 is used as the fluid machinery that controls circulation of the fluid. That is, step S120 (coating agent step) includes the circulation step that circulates the fluid between the inside and the outside of the gas cell 11 through the through-hole 71 using the pump 100 that controls the circulation of the fluid. The coating agent is introduced from the gas cell 11 and the metal tube 62 is extracted. Therefore, the gap 72 is formed between the package 12 and the lid 13. In this case, the low melting point glass 60 that forms the gap 72 is used as the first sealing member.

Figure 6:
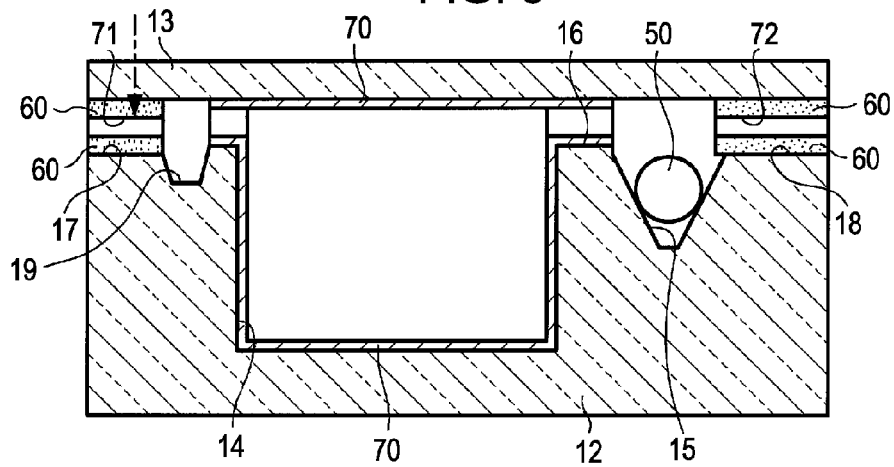
FIG. 6 is a view illustrating a manufacturing step of a gas cell according to the embodiment.
Figure 7:
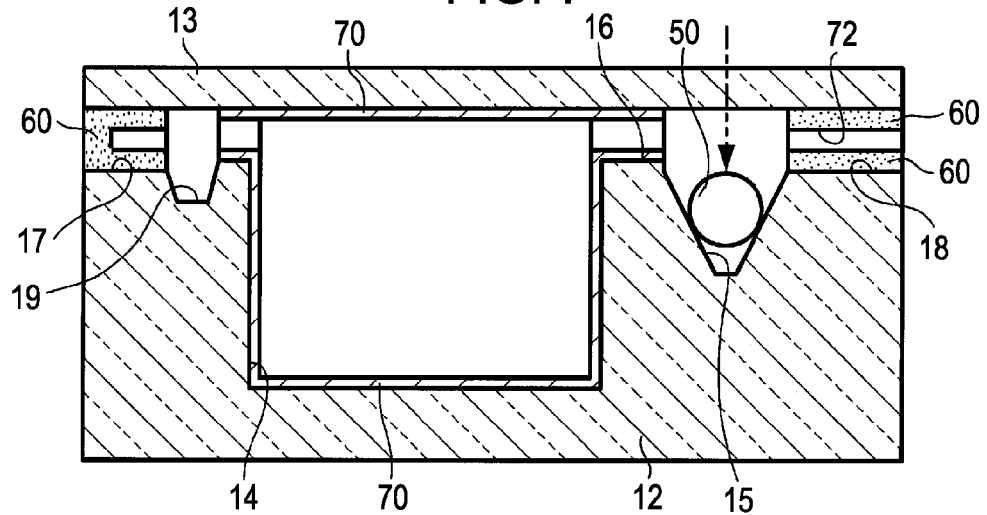
FIG. 7 is a view illustrating a manufacturing step of a gas cell according to the embodiment.

In Step S130 (first sealing step), as shown FIG. 6, under a vacuum environment, laser beam is irradiated to the low melting point glass 60 formed with the through-hole 71 through the lid 13 to heat the low melting point glass 60. Therefore, as shown in FIG. 7, the low melting point glass 60 is melted and the through-hole 71 is sealed. In order to improve the absorption of the laser beams, light absorption materials may be added to the low melting point glass 60.

In step S140 (ampoule destruction step), as shown in FIG. 7, under a vacuum environment, the laser beam is focused on the ampoule 50 such that the laser beam is applied to the ampoule 50 through the lid 13. Therefore, the hole in the ampoule 50 is opened and cleaved, so that the ampoule 50 is destroyed. Thus "destruction" means that a form of the ampoule 50 is destroyed to communicate with the inside and the outside of the ampoule 50. In order to improve the absorption of the laser beams, a film of the light absorption material may be formed on the ampoule 50. In addition, the ampoule 50 may be destroyed by an intense ultrashort laser. The destruction of the ampoule 50 occurs and a vaporized component is generated. The vaporized component is exhausted to the outside from the gap 72. In order to secure a sufficient time in exhausting the vaporized component from the gap 72, a next step S150 (second sealing step) proceeds when the determined time passes after the ampoule 50 is destroyed.

Figure 8:
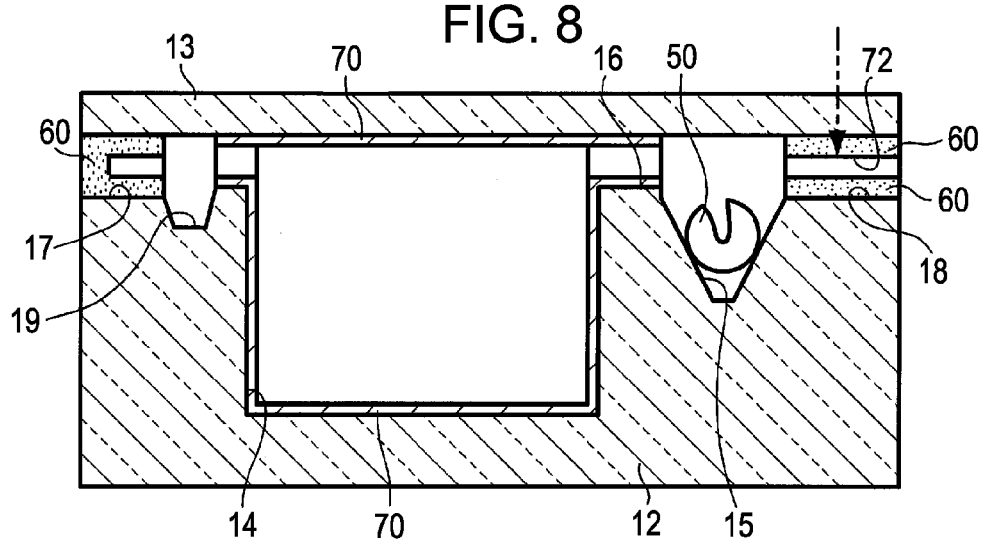
FIG. 8 is a view illustrating a manufacturing step of a gas cell according to the embodiment.
Figure 9:
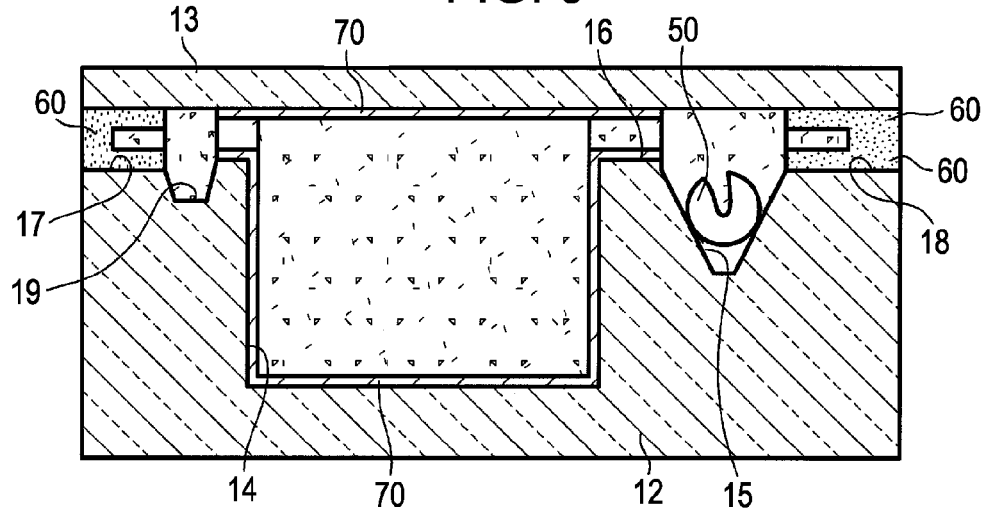
FIG. 9 is a view illustrating a manufacturing step of a gas cell according to the embodiment.

In step S150 (second sealing step), as shown in FIG. 8, under a vacuum environment, the laser beam is irradiated to the low melting point glass 60 that forms the gap 72 through the lid 13 for heating. Therefore, as shown in FIG. 9, the low melting point glass 60 is melted and the gap 72 is sealed.

In step S160 (filling step), the gas cell 11 is filled with the alkali metal gas. Specifically, the alkali metal gas in the ampoule 50 is vaporized by heating the gas cell 11. Therefore, the alkali metal gas is discharged from the ampoule 50. As shown in FIG. 9, the alkali metal gas discharged from the ampoule 50 moves to the main chamber 14 through the groove 16. Therefore, the alkali metal gas is dispersed and the main chamber 14 is filled with the alkali metal gas.

In the invention, since the metal tube 62 protrudes to the outside, it is possible for the pipe 102 of the pump 100 to be connected to the metal tube 62. Therefore, since an inflow or outflow of the cleaning solvent and the coating agent are formed by the pump 100, the time that performs the inflow or the outflow of the cleaning solvent and the coating agent can be reduced compared with a case where the pump 100 is not used. In addition, the through-hole 71 and the gap 72 are both formed at the low melting point glass 60 of the melting point by a normal glass. For this reason, the through-hole 71 and the gap 72 can be sealed even if the through-hole 71 and the gap 72 are heated to a lower temperature than a case where they are made of normal glass. That is, according to the invention, the cleaning solvent and the coating agent may be easily circulated between the inside and the outside of the glass cell 11 to seal the gas cell 11.

In addition, in the invention, the cleaning solvent and the coating agent is circulated within the gas cell 11 by the operation of the pump 100. However, during or after the operation of the pump 100, there is a case that the cleaning solvent and the coating agent enter the through-hole 77 of the metal tube 62. In a such case, if there is no metal tube 62, the cleaning solvent and the coating agent are attached to the inner wall of the low melting point glass 60 used as the sealing member. Accordingly, when the low melting point glass 60 is melted to seal the gap 72, the cleaning solvent and the coating agent are mixed with the low melting point glass 60, so that the sealing effect deteriorates. However, according to the invention, even in this case, since the cleaning solvent and the coating agent enter the through-hole 77 of the metal tube 62, the cleaning solvent and the coating agent are not attached to the low melting point glass 60 used as the sealing member. Therefore, when the gap 72 is sealed, since the low melting point glass 60 is mixed with the cleaning solvent and the coating agent, reliability of the sealing improves.

2. MODIFIED EXAMPLE

The invention is not limited to the embodiment and various modified embodiments can be made. A combination of two or more modified examples as described below may be used.

1. Modified Example 1

In the above-mentioned embodiment, the sealing member having the through-hole 71 was formed by the low melting point glass 60 using the metal wire 61. However, a cylindrical sealing member 81 having a pre-through-hole 73 may be used instead of the sealing member. At this time, the sealing member 81 is used as a second sealing member. A configuration of the gas cell 11 according to the modified example 1 has substantially the same configuration described in the embodiment. However, the concavity 19 is not provided in the package 12.

Figure 10:
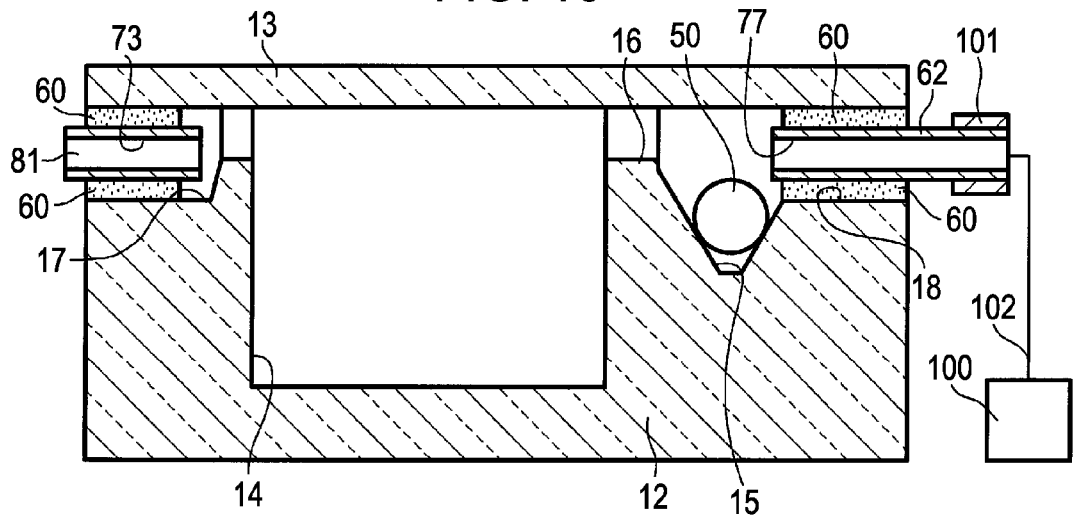
FIG. 10 is a view illustrating a manufacturing step of a gas cell according to a modified example 1.

FIGS. 10 to 15 are views illustrating a manufacturing step of the gas cell 11 according to the modified example 1 described above. In the above-mentioned step S110 (connection step), as shown in FIG. 10, the groove 17 of the package 12 is formed with the cylindrical sealing member 81 instead of the metal wire 61. The sealing member 81 is formed by using a material such as the low melting point glass, solder and the like having a higher melting point than the low melting point glass 60 applied to the lid 13 and the package 12. Herein, it is assumed that the melting point of the low melting glass 60 has a temperature T1 (first temperature) and the melting point of the material that forms the sealing member 81 has a temperature T2 (second temperature). In this case, when the package 12 and the lid 13 are connected each other, only the low melting point glass 60 heated equal to or higher than the temperature T1 and less than the temperature T2 and applied to the package 12 and the lid 13 is melted. Since the heating temperature described above is lower than the melting point of the sealing member 81, the sealing member 81 keeps a cylindrical shape without melting.

Figure 11:
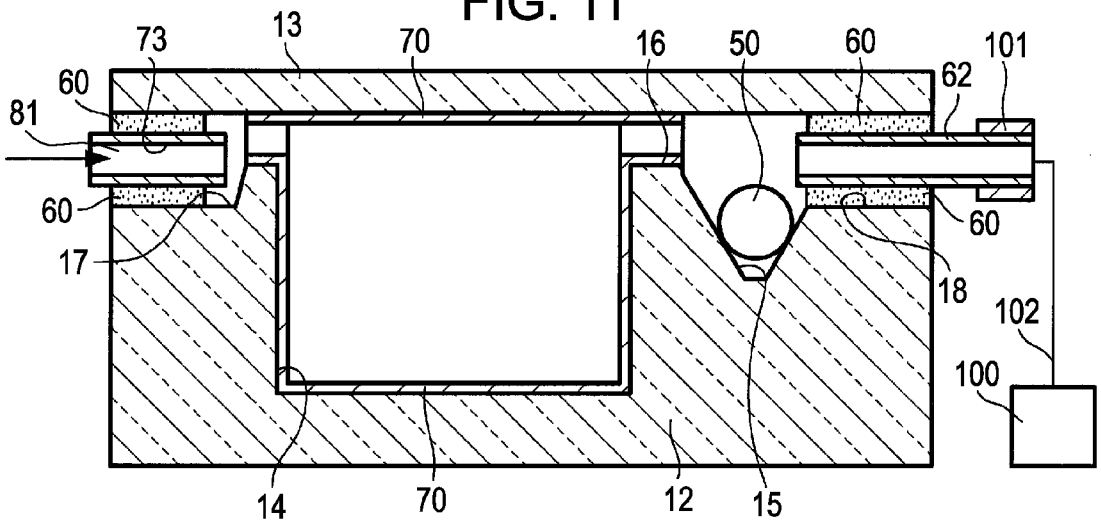
FIG. 11 is a view illustrating a manufacturing step of a gas cell according to a modified example 1.
Figure 12:
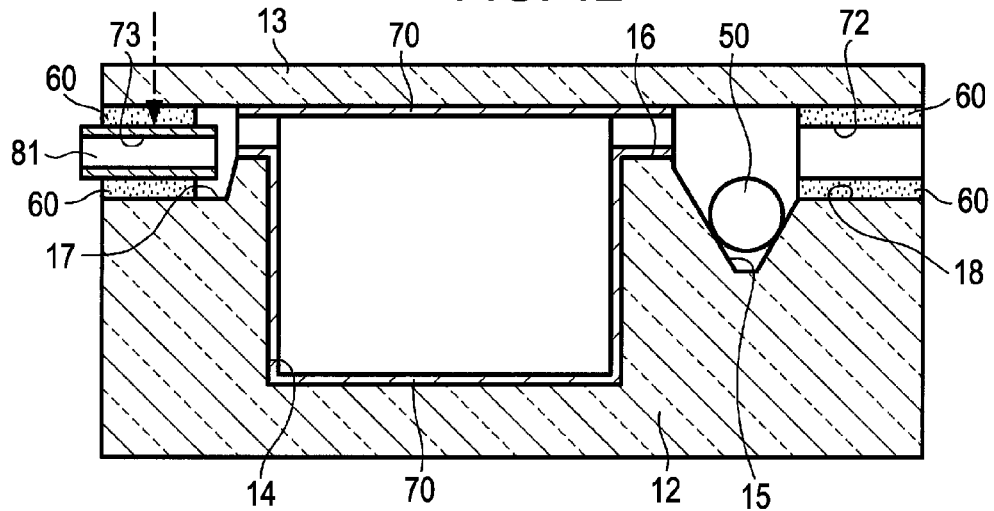
FIG. 12 is a view illustrating a manufacturing step of a gas cell according to a modified example 1.

In step S120 (coating agent step), as shown in FIG. 11, the cleaning solvent and the coating agent flow in and out through the through-hole 73 of the cylindrical sealing member 81. In the above-mentioned step 130 (first sealing step), as shown in FIG. 12, the low melting glass 60 and the sealing member 81 is heated above temperature T2 through irradiation with laser beams. Therefore, the low melting point glass 60 and the sealing member 81 is melted and the through-hole 73 is sealed. The other step is the same step as the above-mentioned embodiments. Therefore, the description thereof will be omitted.

2. Modified Example 2

A gas cell array 10 is not limited to a plurality of gas cells 11 that is simply formed in parallel.

Figure 16:
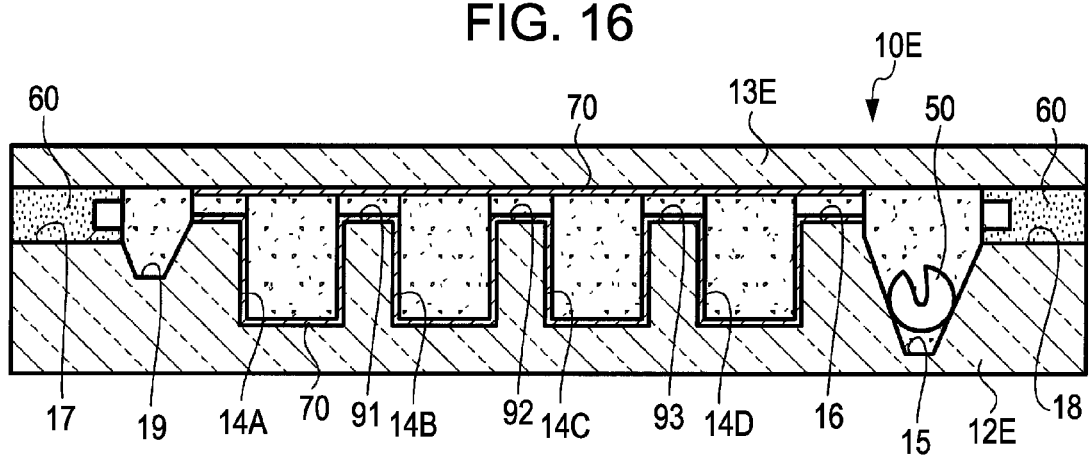
FIG. 16 is a plan view of a gas cell array according to a modified example 2.

FIG. 16 is a cross-sectional view taken along XVI-XVI of the gas cell array E according to the modified example 2. The gas cell array 10E has the same configuration as the configuration in which a plurality of main chambers 14 are provided on the gas cell 11. The gas cell array 10E includes a package 12E and a lid 13E. The package 12E has four main chambers 14A to 14D. The upper of the package 12E is formed with grooves 91 to 93, in addition to concavity 15 and 19 and grooves 16 to 18 described above. The groove 91 connects a main chamber 14A to a main chamber 14B. The groove 92 connects the main chamber 14B to the main chamber 14C. The groove 93 connects the main chamber 14C to the main chamber 14D. A concavity 15 is formed adjacent to a main chamber 14D. A groove 17 is formed to be directed toward the outside from the main chamber 14A. In the gas cell array 10E, an alkali metal gas discharged from ampoule 50 moves to the main chamber 14D through the groove 16. Next, the alkali metal gas moves to the main chambers 14C, 14B and 14A via grooves 93, 92 and 91 in this order. Therefore, the main chambers 14A to 14D are filled with the alkali metal gas.

In addition, in the gas cell array 10, a group including a plurality of gas cells and dummy cells may be disposed on xy plane of two dimensions (disposed in matrix).

Figure 17:
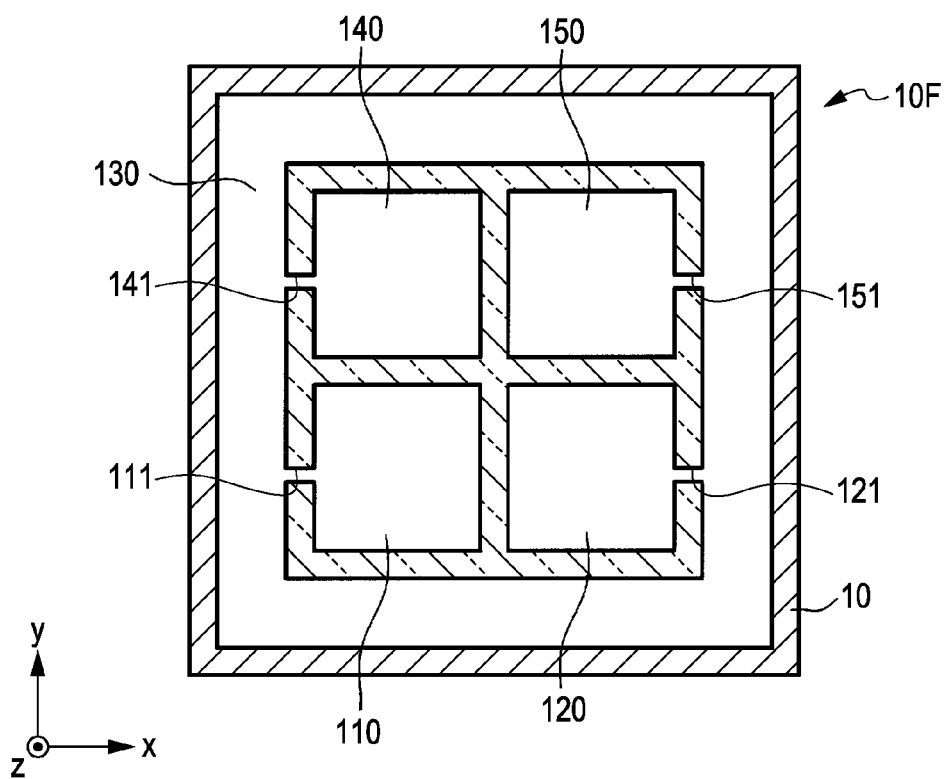
FIG. 17 is a cross-sectional view showing according to a gas cell array according to a modified example 2.

FIG. 17 is a cross-sectional view showing the gas cell array 10F according to the modified example 2. The cross-sectional view is parallel with the xy plane shown. The gas cell array 10F includes a gas cell 110, a gas cell 120, a gas cell 140, a gas cell 150 and a dummy cell 130. A through-hole 111 is disposed between the gas cell 110 and the dummy cell 130. A through-hole 121 is disposed between the gas cell 120 and the dummy cell 130. A through-hole 141 is disposed between the gas cell 140 and the dummy cell 130. A through-hole 151 is disposed between the gas cell 150 and the dummy cell 130. The ampoule 50 accommodates the dummy cell 130. The alkali metal gas discharged from the ampoule 50 disperses from the dummy cell 130 through the through-hole 111, the through-hole 121, the through-hole 141 and the through-hole 151 to the gas cell 110, the gas cell 120, the gas cell 140 and the gas cell 150.

The top of the dummy cell 130 is formed with a groove 17 and the groove 18 that direct toward the outside from the dummy cell 130, similarly to the gas cell 11 shown FIG. 2. However, since FIG. 17 is a cross-sectional view, the groove 17 and the groove 18 are not shown. The groove 17 and the groove 18 are disposed at opposed positions. In addition, in the gas cell array 10F, since the ampoule 50 is disposed in the dummy cell 130, it is not important to provide the concavity 15. The method that seals the gas cell array 10F has the same method that seals the gas cell 11 described above.

3. Modified Example 3

The positions of groove 17 and groove 18 are not limited to those FIG. 2.

Figure 18:
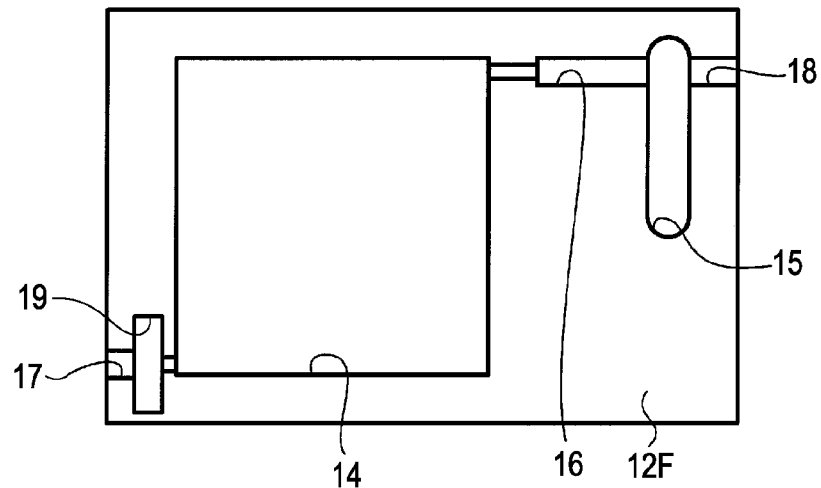
FIG. 18 is a plan view of showing a package according to a modified example 3.

FIG. 18 is a plane view of a package 12F according to the modified example 3. The main chamber 14 shown in FIG. 18 has a rectangular parallelepiped shape. In this case, in an angle of the main chamber 14, it is easy for the spin polarization of the alkali metal atom to be alleviated. Therefore, the groove 17 and the groove 18 may be provided at opposed angles of the main chamber 14 in the upper face of the package 12F. In addition, the grooves 17 and 18 shown in FIG. 18 are formed to extend in parallel with the side surface of the gas cell 11, but may be formed to extend toward an angle of the gas cell 11 of the main chamber 14.

4. Modified Example 4

In the above mentioned embodiment, the pump 100 is used in both sides when the cleaning solvent and the coating agent are caused to flow in and out. However, as described above, when gas cell 11 is disposed within the cleaning solvent and the coating agent in a direction in which through-hole 71 falls down, even if the pump 100 may not be also used, the cleaning solvent and the coating agent flow down from the through-hole 71. Therefore, the pump 100 may be used only when the cleaning solvent and the coating agent are flown in.

5. Modified Example 5

The other end of the metal tube 62 may be disposed to protrude into the groove 16. As shown in FIG. 2, a diameter of the end of the main chamber 14 side of the groove 16 become smaller than that of the concavity 15 side. In this case, the other end of the metal tube 62 may be disposed in the portion of the groove 16 having a larger inner diameter. Therefore, the gas in the main chamber 14 efficiently flows out or the air compressed in the main chamber 14 efficiently flows in.

6. Modified example 6

If the vaporized component from the ampoule 50 which is not discharged and the vaporized component discharged from the ampoule 50 is a small enough amount not to exert an influence, there are cases where it is not necessary that the vaporized component flow out to the outside from the ampoule 50. In this case, step S150 (second sealing step) is performed prior to performing step S140 (ampoule destruction step). For example, step S150 (second sealing step) may be performed while extracting the metal tube 62 in step S120 (coating agent step).

Figure 19:
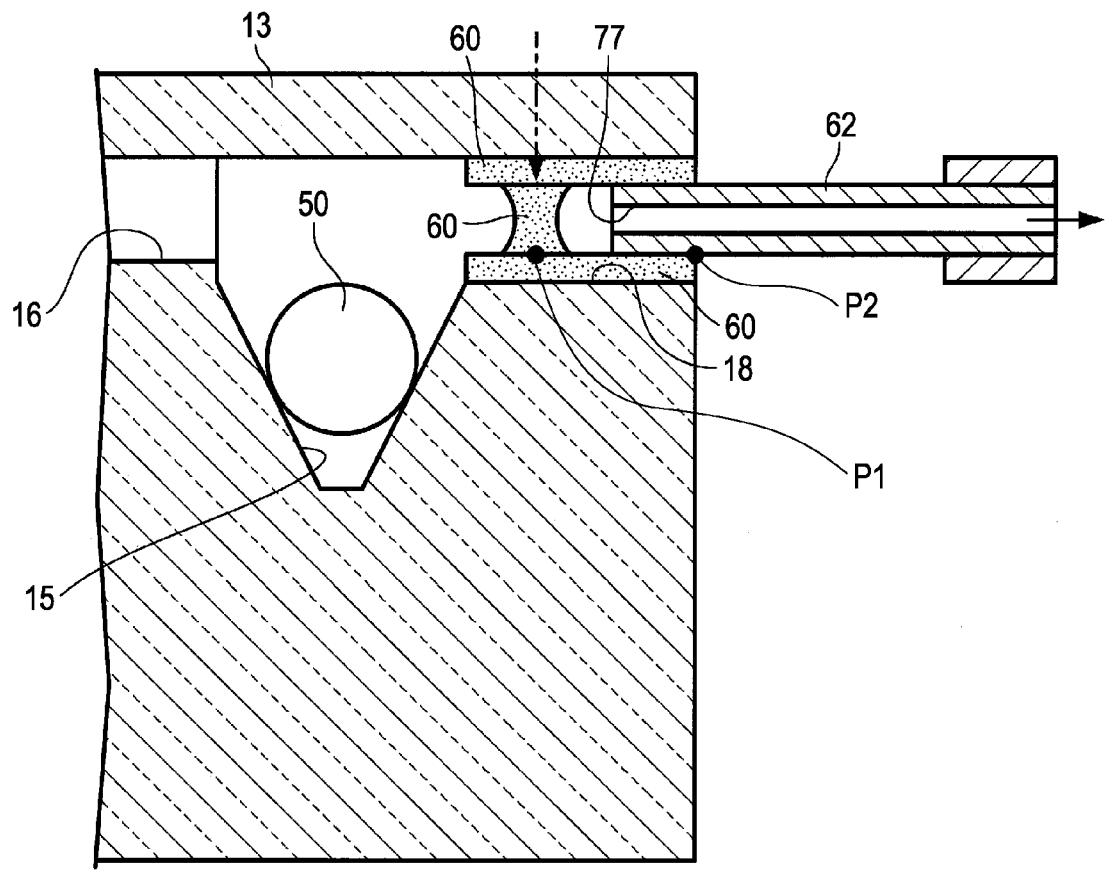
FIG. 19 is a view showing a step S150 (a second sealing step) according to a modified example 6.

FIG. 19 is a view illustrating step S150 (second sealing step) according to the modified example 6. In step S150 (second sealing step), the metal tube 62 is first extracted between a position P1 in which the laser beam is irradiated and a position P2 of the end opening to the outside of the groove 18. Next, in the position P1, the laser beams are applied to the low melting point glass 60 for heating. The gap 72 formed when the low melting point glass 60 melted to extract the metal tube 62 is sealed in advance. After this, the metal tube 62 is extracted. Accordingly, by sealing the gap 72 prior to extracting the metal tube 62 completely, the film 70 is formed in the inside of the main chamber 14 by the coating agent and then airtightness in the gas cell 11 is maintained. Therefore, the film 70 formed at the inside of the gas cell 11 does not in contact with ambient air. In addition, in this case, when the gap 72 is sealed, the entire gas cell 11 may be heated by the annealing oven.

7. Modified Example 7

The shape of the gas cell 11 is not limited to the shape shown in FIG. 2. The gas cell 11 shown in FIG. 2 has a rectangular parallelepiped shape. However, the shape of the gas cell 11 has a curved surface on a portion of a polyhedron, a sphere, a columnar and the like in addition to the rectangular parallelepiped.

8. Modified Example 8

In the embodiment, the low melting point glass is used as the connection material connecting the package 12 and the lid 13. However, the connection material is not limited to the low melting point glass. For example, the connection material may be solder. The package 12 and the lid 13 may be connected by an optical contact. In this case, the connection material is coated only to the grooves 17 and 18. In addition, the connection material may be applied to both the package 12 and the lid 13 or may be applied to only the top surface of the package 12 or the lower surface of the lid 13. In this case, the low melting point glass 60 used as the sealing member is disposed only either between the metal tube 62 and the package 12 or between the metal tube 62 and the lid 13. Even in this case, if the amount of the low melting point glass 60 is sufficient, the gap 72 formed after the metal tub 62 is extracted is sealed by melting the low melting point glass 60.

9. Modified Example 9

In the above-mentioned embodiment, the cylindrical metal tube 62 formed using nickel is used as a tubular member disposed between the package 12 and the lid 13. However, the shape is not limited to the tubular shape. For example, the tubular member may have a tubular shape which is the shape of a triangle, a quadrangle and the like other than a circle in a cross-sectional view. For example, the material of the tubular member is not limited to nickel. For example, the tubular member may be formed using the material other than nickel. However, the tubular member may be formed using the connection material used to connect the package 12 and the lid 13 and the material which is not readily connectable thereto.

10. Modified Example 10

The shape of the sealing member is not limited to the cylindrical shape having the through-hole. For example, the shape of then sealing member may have a three-dimensional shape other than a cylindrical shape having the through-hole such as a polyhedron, a cube or a rectangular parallelepiped, a sphere and a column. In this case, in the embodiment, the groove 17 matching the shape of the sealing member is formed. In the modified example 1, the sealing member 81 having the above-mentioned shape is used. Further, the material of the sealing member is not limited to the low melting point glass or solder. For example, the material may be a resin.

11. Modified Example 11

In the above-mentioned embodiment, the metal wire 61 formed using nickel was used as the rod-shaped member disposed between the package 12 and the lid 13. However, the rod-shaped member is not limited to the metal wire 61 formed using nickel. For example, nickel plating may be performed on the rod-shaped member formed using a material other than nickel. The rod-shaped member may be formed using the connection material used to connect the package 12 and the lid 13 each other and a material which is not readily connectable thereto.

12. Modified Example 12

The alkali metal atom may be introduced into the gas cell 11 in any form of a solid, liquid or gas. It is not necessary that the alkali metal atom be in gas form all the time except for without being gasified at least at the time of measurement.

13. Modified Example 13

An application of the gas cell 11 is not limited to a magnetic sensor. For example, the gas cell 11 may be used in an atom oscillator.

14. Modified Example 14

The package that is sealed using a method for sealing the package according to the invention is not limited to the gas cell 11. For example, a hermetically sealed package may be used in an electronic device of a gyroscope using a crystal or a micro electro mechanical system (MEMS), an acceleration sensor, a pressure sensor, a slant sensor, a crystal oscillator and the like. The method for sealing the package according to the invention may be used for sealing the hermetically sealed package. Particularly, the method for sealing the package is the same method as the above-mentioned embodiment and the modified example. The tubular member having the through-hole is disposed between the hermetically sealed package and the lid and with one end of the tubular being formed to protrude the outside, the sealing member is disposed between the tubular and the package or lid to connect the package and the lid. The end of the tubular member is connected to the fluid machinery controlling circulation of the fluid. The fluid machinery introduces the fluid between the inside and outside of the package through the through-hole. The gap between the package and the lid formed when the tubular member is extracted by melting extracting and sealing member is sealed. The fluid machinery may be, for example, a vacuum pump.

The entire disclosure of Japanese Patent Application No. 2011-186420, filed Aug. 29, 2011 and No. 2012-132708, filed Jun. 12, 2012 are expressly incorporated by reference herein.

What is claimed is:

1. A method for sealing a package comprising:
   connecting a package and a lid by disposing a reception section receiving alkali metal atom within the package having an opening, providing a tubular member having a first through-hole between the package and the lid covering the opening, one end of the tubular member protruding to the outside, providing a first sealing member between the tubular member and the package or the lid, and providing a second sealing member having a second through-hole between the package and the lid;
   circulating a coating agent by connecting fluid machinery to the one end of the tubular member to control circulation of fluid, introducing the coating agent into the inner face of the package via the second through-hole using the fluid machinery, forming film on the inner face of the package using the coating agent, and exhausting the coating agent provided in the inside of the package to the outside via the second through-hole using the fluid machinery;
   sealing a gap between the package and the lid formed when the tubular member is extracted by extracting the tubular member and melting the first sealing member, and sealing the second through-hole by melting the second sealing member; and
   destroying the reception section by applying a laser beam to the reception section.

2. The method for sealing a package according to claim 1, wherein in the circulating the coating agent, the second through-hole is disposed in the coating agent and when the coating agent is introduced, the fluid machinery discharges gas within the package to the outside from the first through-hole to decrease pressure within the package.

3. The method for sealing a package according to claim 2, wherein, in the circulating the coating agent, when the coating agent is discharged, the fluid machinery introduces compressed gas through the first through-hole into the inner side of the package to increase pressure within the package.

4. The method for sealing a package according to claim 1, wherein, in the connecting the package and the lid, a surface that connects the package and the lid is coated with a connection material, a rod-shaped member is disposed between the package and the lid, one end of the rod-shaped member being formed to protrude outward, the package and the lid are connected by the connection material being melted, and the second sealing member is formed by the connection material by extracting the rod-shaped member after cooling.

5. The method for sealing a package according to claim 1, wherein in the connecting the package and the lid, a surface that connects the package and the lid is coated with a connection material having a melting point of a first temperature, the second sealing member is formed with a material having a melting point of a second temperature higher than the first temperature, the connection material is heated at a temperature equal to or higher than the first temperature and less than the second temperature and the package and the lid are connected by melting the connection material, and in sealing the gap, the second sealing member is heated at a temperature equal to or higher than the second temperature.

* * * * *